United States Patent [19]

Michelotti et al.

[11] Patent Number: 5,075,471

[45] Date of Patent: Dec. 24, 1991

[54] INSECTICIDAL FERROCENOYL ACYLHYDRAZINES

[75] Inventors: Enrique L. Michelotti, Fort Washington; Dat P. Le; Glenn R. Carlson, both of North Wales; Anne R. Egan, Fort Washington, all of Pa.

[73] Assignee: Rohm and Haas Company, Philadelphia, Pa.

[21] Appl. No.: 595,072

[22] Filed: Oct. 9, 1990

[51] Int. Cl.$^5$ .............................................. C07F 15/02
[52] U.S. Cl. ..................................... 556/144; 556/143
[58] Field of Search ................. 556/144, 143; 514/502

[56] References Cited

U.S. PATENT DOCUMENTS

| | | | |
|---|---|---|---|
| 3,751,441 | 8/1973 | Van Landuyt | 556/144 X |
| 3,853,943 | 12/1974 | Webster | 556/144 X |
| 3,950,373 | 4/1976 | Nesmeyanov et al. | 556/144 X |
| 3,960,911 | 6/1976 | Suschitzky et al. | 556/144 X |

OTHER PUBLICATIONS

Ratajczak et al., CA 99, 5768 (1983), p. 528.
Ogierman, CA 103, 18351 (1985), p. 208.

*Primary Examiner*—Arthur C. Prescott

[57] ABSTRACT

Insecticidal compounds of the formula

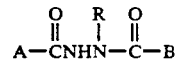

wherein one of A or B is ferrocenyl and the other of A or B is phenyl or substituted phenyl and R is branched alkyl are effective in controlling the Southern Armyworm and Mexican Bean Beetle.

18 Claims, No Drawings

INSECTICIDAL FERROCENOYL ACYLHYDRAZINES

BACKGROUND OF THE INVENTION

This invention relates to novel N-ferrocenoyl-N'-acylhydrazines which are useful as insecticides, compositions containing these compounds and methods of their use.

Compounds of the present invention are particularly suitable for controlling plant-destructive insects in crops of cultivated plants, ornamentals and forestry.

Certain acyl hydrazine derivatives have been disclosed in the literature.

In *Sint Metody Osnt Elemtoorg, Soedin*, 66-9, 1982, edited by I. Lapkin, (in Russian, CA: 100(1):6778) certain ferrocenoyl hydrazine compounds are disclosed; no biological data are given.

In *J. Prakt. Chem.* 35(3-4) 149-58 (1967), Larkowski, H. J.; Pannier, R. and Wende, A. (in German) certain ferrocenoyl hydrazine compounds are disclosed; no biological activity is disclosed.

EP 232-075-A (1987), AU 8664-289-A (1987), and EP 228-564-A (1987) disclose diacyl-N-substituted hydrazines and their insecticidal use.

Certain ferrocene pyrethroid compounds are disclosed as insecticides in CA: 99: 5768 (1983) and CA: 103: 18351 (1985).

The biological applications of ferrocene compounds are reviewed in *J. Organometalic Chem.;* 278, 314–17 (1984) and CA: 110: 149718.

The ferrocenyl acylhydrazines of the present invention differ from known compounds primarily by their ferrocenoyl substituent and/or the branched alkyl substituents on the nitrogen atom.

Compounds of the present invention are also distinguished by their excellent insecticidal activity, particularly against insects of the orders Lepidoptera and Coleoptera, and most particularly against insects of the order Lepidoptera, without material adverse impact on beneficial insects.

SUMMARY OF THE INVENTION

In accordance with the present invention, there are provided insecticidal compounds, compositions and methods of using such compounds and compositions wherein the compositions comprise an agronomically acceptable carrier and an insecticidally effective amount of, or from about 0.0001% to about 99% by weight of the composition.

The present invention comprises a compound represented by the general formula:

(I)

wherein

A and B are independently selected from ferrocenyl, phenyl or phenyl optionally substituted with up to three substituents independently selected from ($C_1$-$C_6$) alkyl, ($C_1$-$C_6$) haloalkyl, ($C_1$-$C_6$) alkoxy, ($C_1$-$C_6$) haloalkoxy, or halogen; and with the proviso that one and only one of A and B must be ferrocenyl; and R is branched ($C_3$-$C_6$) alkyl.

In a preferred embodiment, this invention comprises a compound of formula I wherein:

A and B are independently selected from ferrocenyl, phenyl or phenyl optionally substituted with up to two substituents independently selected from ($C_1$-$C_6$) alkyl or halogen; and R is isobutyl, sec-butyl, tert-butyl, or neopentyl and with the proviso that one and only of A and B must be ferrocenyl.

In a more preferred embodiment, this invention comprises a compound of formula I wherein A and B are independently selected from ferrocenyl, phenyl or phenyl optionally substituted with up to two substituents independently selected from methyl and halogen and R is tert-butyl; and with the proviso that one and only one of A and B must be ferrocenyl.

In the most preferred embodiment, this invention comprises a compound selected from the group of N-ferrocenoyl-N'-3-methylbenzoyl-N'-t-butylhydrazine; N-2,3-dimethylbenzoyl-N'-ferrocenoyl-N'-t-butylhydrazine; and N-ferrocenoyl-N'-2-bromobenzoyl-N'-t-butyhydrazine.

In another aspect, this invention comprises a pesticidal composition comprising a pesticidally effective amount of the compound of formula (I) of this invention defined herein above and an agronomically acceptable inert carrier.

In yet another aspect, this invention comprises a method of controlling pests such as insects, especially the Armyworm and Mexican Bean Beetle, which comprises applying to said pest or to the soil or to the foliage of plants to be freed from infestation, a pesticidally effective amount of a compound having the formula (I) defined herein above.

The term "halo" by itself or as a part of another substituent includes chloro, fluoro, bromo and iodo.

The term "alkyl" by itself or as a part of another substituent, unless otherwise stated, includes straight and branched chain groups such as methyl, ethyl, n-propyl, isopropyl, n-butyl, isobutyl, sec-butyl, tert-butyl, n-pentyl, neopentyl, hexyl, and the like.

The term "haloalkyl" by itself or as a part of another substituent is an alkyl group of the stated number of carbon atoms having one or more halo atoms bonded thereto such as but not limited to chloromethyl, bromoethyl, trifluoromethyl and bromodifluoromethyl.

The term alkoxy includes, but is not limited to groups such as methoxy, ethoxy, isoproxy, t-butoxy, isobutoxy, neopentoxy and the like. The term haloalkoxy refers to mono or poly halogen substituted alkoxy groups such as trifluoromethoxy, 2-chloroethoxy, trifluoromethoxy, 3-bromopropoxy, and the like.

The term "pesticidally or insecticidally effective amount" means a quantity of compound which causes a reduction of the pest or insect population or decreases crop damage compared to a control group.

In certain cases the compounds of this invention possess asymmetric centers which give rise to optical enantiomorphs and diastereomers. The compounds may also possess acidic or basic moieties which may form salts or metal complexes; this invention includes such enantiomorphs, salts and metal complexes.

The compounds of this invention may be prepared by a variety of conventional reaction schemes.

Methods particularly useful for preparing the compounds are illustrated is the following reaction sequences wherein A, B and R are as defined in formula I, above.

PROCESS A

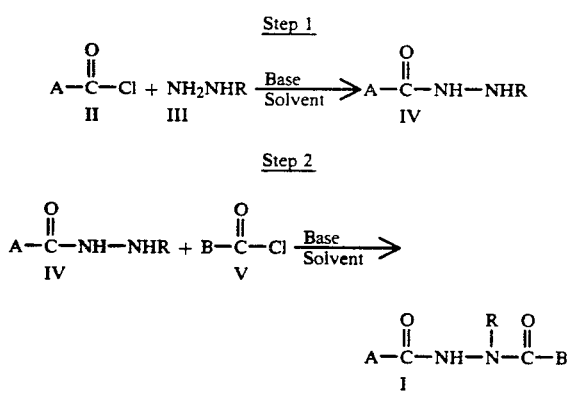

Ferrocenoyl chloride, for example Formula V where B is ferrocencyl, may be prepared by the reaction of ferrocene carboxylic acid which is commercially available from Aldrich Chemical Co., 1001 W. Saint Paul Ave., Milwaukee, Wis. 53223, with a suitable chlorinating agent such as oxalyl chloride, phosgene, thionyl chloride, and the like in an inert solvent at temperature of about $-20°$ C. to $100°$ C. for 1 to 8 hours.

In process A, a compound of Formula II is reacted with a monosubstituted hydrazine of Formula III or a corresponding acid addition salt such as the hydrochloride salt or the like in the presence of a base in an inert or substantially inert solvent or mixture of solvents to afford an intermediate product of Formula IV which can be isolated or further reacted with a compound of Formula V in the presence of a base in an inert or substantially inert solvent or mixture of solvents to afford the desired product of Formula I.

Examples of the compounds of Formula II and/or Formula V which can be used in the above processes include ferrocenoyl chloride, benzoyl chloride, 4-chlorobenzoyl chloride, 4-methylbenzoyl chloride, 3,5-dichlorobenzoyl chloride, 2-bromobenzoyl chloride, and the like. The compounds of Formula II and/or Formula V are generally commercially available or can be prepared by known procedures.

Examples of the compounds of Formula III which can be used in the above processes include iso-propylhydrazine, t-butylhydrazine, neopentylhydrazine, isobutylhydrazine, isopentylhydrazine, isohexylhydrazine, and the like. The compounds of Formula III are generally commercially available or can be prepared by known procedures. For example, the addition of an alkene to hydrazine with an acid catalyst as described in U.S. Pat. No. 4,954,655 affords the monosubstituted hydrazine of Formula III.

Suitable solvents for use in the above processes include water; alcohols such as methanol, ethanol, isopropanol and the like; hydrocarbons such as toluene, xylene, hexane, heptane and the like; glyme; tetrahydrofuran; acetonitrile; pyridine; or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide; or potassium hydroxide.

Preferred bases are sodium hydroxide, potassium hydroxide or triethylamine.

Process B can also be used when preparing compounds according to Formula I where A and B are as defined above for Formula I and R comprises $R^3CHR^4$ wherein $R^3$ is hydrogen or lower alkyl and $R^4$ is lower alkyl; W is a good leaving group such as halo, for example, chloro; an alkoxy, for example, ethoxy; methyl sulfonate ($-OSO_2CH_3$); or an ester, for example, acetate ($-OC(O)CH_3$).

PROCESS B

Method 1

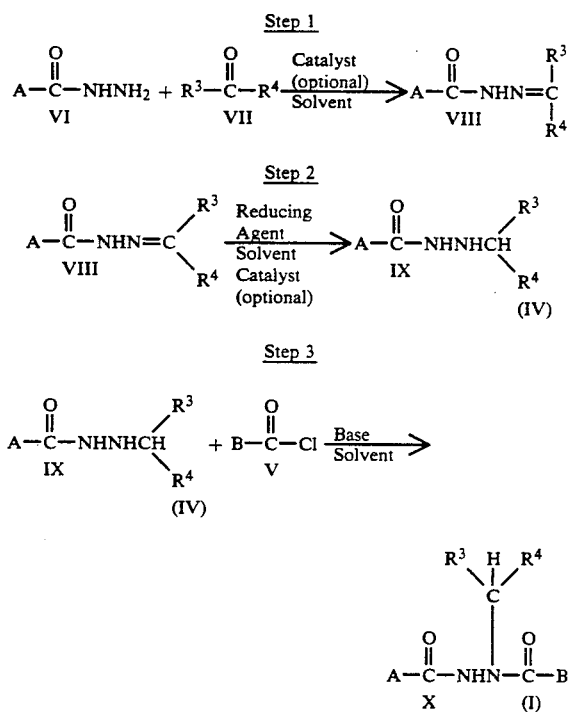

Method 2

$$A-\overset{O}{\overset{\|}{C}}-W + H_2N-\overset{}{\underset{R}{N}}-\overset{O}{\overset{\|}{C}}-B \xrightarrow[\text{Solvent}]{\text{Base}}$$
$$\text{XI} \qquad \text{XII}$$

$$A-\overset{O}{\overset{\|}{C}}-\underset{H}{N}-\underset{R}{N}-\overset{O}{\overset{\|}{C}}-B$$
$$\text{I}$$

In Process B, Method 1, a compound of Formula VI is reacted with a ketone or aldehyde of Formula VII in an inert or substantially inert solvent or mixture of solvents and optionally in the presence of a catalyst to afford an intermediate product of Formula VIII. The intermediate product of Formula VIII is then further reacted with a reducing agent in an inert or substantially inert solvent or mixture of solvents to afford a second intermediate product of Formula IX (IV) which can be isolated or further reacted with a compound of Formula V in the presence of a base in an inert or substantially inert solvent or mixture of solvents to afford the desired product of Formula X (I).

Examples of the compounds of Formula VI which can be used in the above Process B, Method 1, include ferrocenoyl-hydrazine, benzoylhydrazine, 4-chlorobenzoylhydrazine, 2-methylbenzoylhydrazine, 4-methylbenzoylhydrazine, 3,5-dichlorobenzoylhydrazine and the like. The compounds of Formula VI are generally commercially available or can be prepared by known procedures.

Examples of the compounds of Formula VII which can be used in the above Process B, Method 1, include methylethylketone, diethylketone and the like. The compounds of Formula VII are generally commercially available or can be prepared by known procedures.

Optionally, a catalyst may be used in Step 1, Method 1 of Process B. Suitable catalysts generally include organic acids such as acetic acid, trifluoroacetic acid, oxalic acid and the like; mineral acids such as hydrochloric acid, sulfuric acid, nitric acid and the like; arylsulfonic acids such as toluenesulfonic acid; or pyridinium toluenesulfonate. Preferred catalysts are organic acids or arylsulfonic acids. Most preferred catalysts are acetic acid or trifluoroacetic acid.

Suitable solvents for use in the above Process B, Method 1, Step 1, include alcohols such as methanol, ethanol, isopropanol and the like; aromatic hydrocarbons such as toluene, benzene; ethers such as tetrahydrofuran (THF), glyme and the like; or dimethylformamide (DMF). Preferred solvents are alcohols and hydrocarbons. Most preferred solvents are alcohols such as methanol or ethanol.

Examples of suitable reducing agents for use in the above Process B, Method 1, Step 2, include hydrides such as sodium borohydride and derivatives thereof such as sodium cyanoborohydride, lithium aluminum hydride and derivatives thereof and the like; or diborane. Preferred reducing agents are sodium borohydride and derivatives thereof or lithium aluminum hydride and derivatives thereof. Most preferred as a reducing agent is sodium cyanoborohydride.

Optionally, in Process B, Method 1, Step 2, a catalyst may be included. Examples of suitable catalysts include organic acids such as acetic acid, trifluoroacetic acid; or mineral acids such as hydrochloric acid, sulfuric acid and the like. Preferred catalysts are organic acids or hydrochloric acid. Most preferred catalysts are acetic acid, trifluoroacetic acid or hydrochloric acid.

Suitable solvents for use in the above Process B, Method 1, Step 2, include alcohols such as methanol, ethanol, isopropanol and the like; ethers such as tetrahydrofuran (THF), diethylether, glyme and the like; or halohydrocarbons such as methylene chloride, chloroform and the like. Preferred solvents are alcohols and most preferred are methanol or ethanol.

Step 3 of Process B, Method 1 corresponds to Step 2 of Process A. Consequently, those bases and solvents suitable for use in Step 2 of Process A are suitable for use in Step 3, Method 1 of Process B including the preferred bases and solvents described above.

In Process B, Method 2, N'-substituted-N'-benzoylhydrazine of Formula XII is reacted with a compound of Formula XI for example ferrocenoyl chloride, in the presence of a base in an inert or substantially inert solvent or mixture of solvents to afford the desired product of Formula I.

The compounds of Formula XI are generally commercially available or can be prepared from commercially available compounds by procedures well known to those skilled in the art as described below.

Examples of the compounds of Formula XII which can be used in the above Process B, Method 2, include N'-t-butyl-N'-benzoylhydrazine; N'-t-butyl-N'-(3-methylbenzoyl)hydrazine; N'-t-butyl-N'-(4-chlorobenzoyl)hydrazine; N'-t-butyl-N'-(2-fluorobenzoyl)hydrazine; N'-isopropyl-N'-benzoylhydrazine; N'-neopentyl-N'-(4-chlorobenzoyl)-hydrazine, and the like.

Suitable solvents for use in the above Process B, Method 2, include water; hydrocarbons such as toluene, xylene, hexane, heptane and the like; alcohols such as methanol, ethanol, isopropanol, and the like; glyme; tetrahydrofuran; acetonitrile; pyridine; or haloalkanes such as methylene chloride; or mixtures of these solvents. Preferred solvents are water, toluene, methylene chloride or a mixture of these solvents.

Examples of bases suitable for use in the above Process B includes tertiary amines such as triethylamine; pyridine; potassium carbonate; sodium carbonate; sodium bicarbonate; sodium hydroxide; or potassium hydroxide. Preferred bases are sodium hydroxide or triethylamine.

The compounds of Formula XII can be prepared by procedures known to those skilled in the art from commercially available reactants. By way of example, a suitably substituted hydrazine (such as t-butylhydrazine) is reacted with an aldehyde or ketone (such as acetone) in the presence of a base (such as triethylamine) to afford a hydrazone which is then reacted with a benzoyl chloride in an inert or substantially inert solvent or mixture of solvents in the presence of a base (such as sodium hydroxide) to afford an N'-substituted-N'-benzoylhydrazone which is then reacted with an acid (such as hydrochloric acid) to afford the compound of Formula XII. Alternatively, a suitable substituted hydrazine (such as t-butylhydrazine) is reacted with di-tert-butyldicarbonate in an inert or substantially inert solvent mixture of solvents (such as toluene/water) to afford an N'-t-butyl-Nt-butoxycarbonylhydrazine which is then reacted with a benzoyl chloride in an inert or substantially inert solvent or mixture of solvents to afford an N'-t-butyl-N'-benzoyl-N-t-butoxycarbonylhydrazine which is then reacted with an acid to afford the desired compound of Formula XII.

Process C can also be used when preparing compounds according to Formula I where A, B and R are as defined for Formula I.

PROCESS C

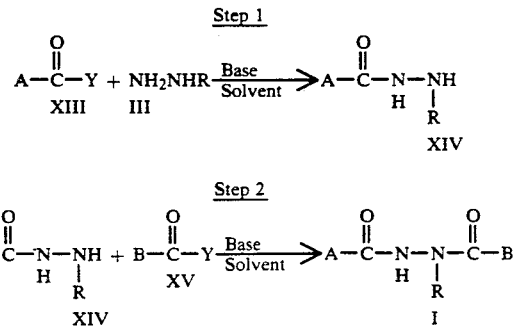

Y is a good leaving group such as carboxyalkylthio (for example, carboxymethylthio, —SCH$_2$CO$_2$H); alkylthio (for example, methylthio); or halo (for example, chloro).

In Process C, a compound of Formula XIII is reacted with a monosubstituted hydrazine or hydrazine hydrate of Formula III or a corresponding acid addition salt such as the hydrochloride salt or the like in the presence of a base in an inert or substantially inert solvent or mixture of solvents to afford an intermediate compound of formula XIV which can be isolated or further reacted with a compound of Formula XV in the presence of a base in an inert or substantially inert solvent or mixture of solvents to afford the desired product of Formula I.

The compounds of Formula XIII and/or Formula XIV are generally commercially available or can be prepared by known procedures.

Suitable solvents for use in the above Process C are generally polar high-boiling solvents such as toluene, DMF, glyme, THF, and pyridine. The preferred solvent is toluene.

Suitable bases for use in the above Process C include tertiary amines such as aqueous sodium hydroxide, aqueous potassium carbonate, triethylamine and pyridine. The preferred base is potassium carbonate.

Process D can also be used when preparing compounds according to Formula I where R, A, and B are as defined above for Formula I, and Z is t-butyl; ethyl; phenyl; or benzyl.

PROCESS D

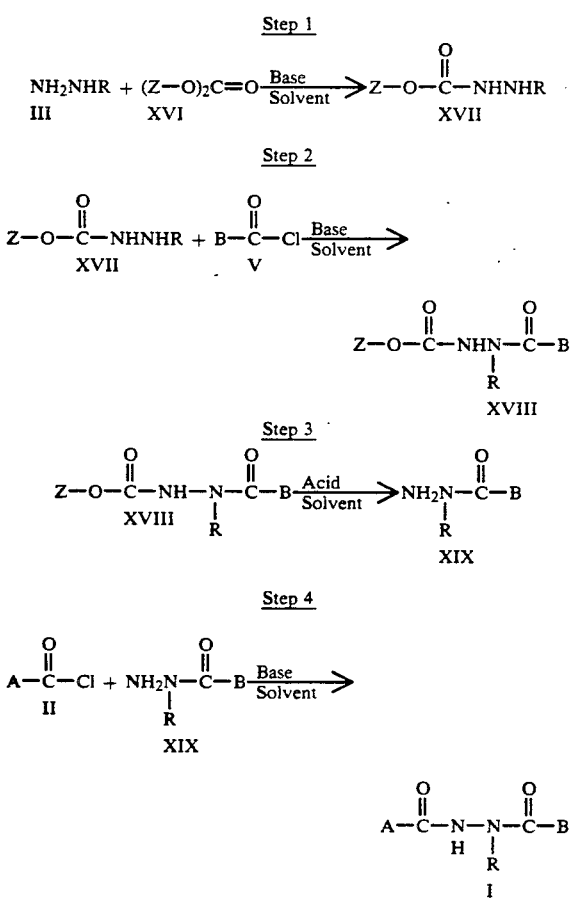

In Process D, a monosubstituted hydrazine or hydrazine hydrate of Formula III or a corresponding acid addition salt, such as the hydrochloride salt or the like, is reacted with a compound of the Formula XVI in the presence of a base in an inert or substantially inert solvent or mixture of solvents to afford an intermediate product of Formula XVII. The intermediate product of Formula XVII is then further reacted with a compound of Formula V in the presence of a base in an inert or substantially inert solvent or mixture of solvents to afford a second intermediate product of Formula XVIII. The second intermediate product of Formula XVIII is then further reacted with an acid in an inert or substantially inert solvent or mixture of solvents to afford a third intermediate product of Formula XIX. The third intermediate product of Formula XIX is then further reacted with a compound of Formula II in the presence of a base in an inert or substantially inert solvent or mixture of solvents to afford the desired product of Formula I.

Examples of the compounds of Formula XVI which can be used in the above Process D include di-t-butylcarbonate, diethylcarbonate, diphenylcarbonate, dibenzylcarbonate and the like. The compounds of Formula XVI are generally commercially available or can be prepared by known procedures.

Suitable solvents for use in the above Process D, Steps 1,2 and 4 include water; THF; dioxane; toluene; alcohols such as methanol, ethanol and isopropanol; hexane; acetonitrile; pyridine; and haloalkanes such as methylene chloride; or mixtures of these solvents.

Preferred solvents are dioxane; toluene; THF; pyridine; methylene chloride or water.

Most preferred solvents are dioxane; water or toluene.

Examples of the bases for use in the above Process D, Steps 1,2 and 4 include tertiary amines such as triethylamine; pyridine; potassium carbonate, sodium carbonate; sodium bicarbonate; sodium hydroxide; and potassium hydroxide.

Preferred bases are sodium hydroxide; potassium hydroxide; pyridine or triethylamine.

Suitable solvents for use in the above Process D, Step 3 include alcohols such as methanol, ethanol and isopropanol; water; THF; dioxane; and acetonitrile.

Preferred solvents are methanol or ethanol.

Examples of acids for use in the above Process D, Step 3 include concentrated hydrochloric acid or concentrated sulfuric acid.

The most preferred processes for the preparation of the compounds of this invention are Process A wherein A is phenyl or substituted phenyl and B is ferrocenyl; and process D wherein B is phenyl or substituted phenyl and A is ferrocenoyl.

The above Processes A and B, Method 1, can be carried out at temperatures between about $-0°$ C. and about 100° C. Preferably, these reactions are carried out between about $-5°$ C. and about 50° C.

The above Process B, Method 2, can be carried out at temperatures between about $-50°$ C. and about 150° C. Preferably when W is a halo radical, the reaction is carried out between about 0° C. and about 30° C. When W is alkoxy, the reaction is preferably carried out between about 100° C. and about 150° C. When W is methyl sulfonate, the reaction is preferably carried out between about $-20°$ C. to about 20° C. When W is an ester, the reaction is preferably carried out between about 0° C. and about 50° C.

Process C can be carried out at temperatures between about 10° C. and 200° C. Preferably, this reaction is carried out between about 70° C. and about 100° C.

Process D can be carried out at temperatures between about 0° C. and 100° C. Preferably, these reactions are carried out between about 0° C. and about 50° C.

Preparation of the compounds of the present invention by processes A, B, C and D is preferably carried out at about atmospheric pressure, although higher or lower pressures can be used if desired.

Substantially equimolar amounts of reactants are preferably used in processes A, B and C, although higher or lower amounts can be used if desired.

Generally, about one equivalent of base is used per equivalent of starting material of Formula II, V, XI and/or XIII. Where the acid addition salt of the monosubstituted hydrazine of Formula III is used, one additional equivalent of base is used. In Process A, when an acid addition salt of the monosubstituted hydrazines of Formula III is used, about two equivalents of base are used in Step 1 and about one equivalent of base is used in Step 2.

Modifications to the above processes may be necessary to accommodate reactive functionalities of particular A and/or B substituents. Such modifications would be apparent and known to those skilled in the art.

It will be appreciated by those skilled in the art that electronic forces may give rise to more than one isomer of the compounds of Formula I such as enantiomers, conformers and the like. There may be a difference in properties such as physical characteristics and degree of biological activity between such isomers. Separation of a specific isomer can be accomplished by standard techniques well known to those of ordinary skill in the art such as silica gel chromatography.

The following examples will further illustrate this invention but are not intended to limit it in any way. In Table I, some ferrocenoyl acyl hydrazines of the present invention that have been made are listed. The structure of these compounds was confirmed by NMR and IR.

EXAMPLE 1

Preparation of N'-t-butyl-N-benzoylhydrazine

To a stirred suspension of t-butylhydrazine hydrochloride (1.24 g, 10 mmol) in toluene (30 ml) at room temperature was added dropwise a 50% aqueous solution of sodium hydroxide (0.8 g, 10 mmole). After 15 min., the reaction mixture was cooled to 5° C. and a solution of benzoyl chloride (1.42 g, 10 mmol) in toluene (5 ml) and a solution of 50% aqueous sodium hydroxide (0.8 g, 10 mmol) were added dropwise simultaneously from separate addition funnels while maintaining the temperature at or below 10°. Following the addition, the reaction mixture was warmed to room temperature and stirred for 1 hr. The reaction mixture was diluted with toluene washed with water. The organic layer was separated, dried over anhydrous magnesium sulfate, and the solvent removed under vacuum to afford a yellow oil which slowly solidified on standing. The product was recrystallized from ethyl ether:-hexane to afford white crystals.

EXAMPLE 2

Preparation of ferrocenoyl chloride

Ferrocene carboxylic acid (5.0 g, 21.7 mmol) was suspended in 40 mL of toluene containing a catalytic amount of DMF; oxalyl chloride (3.08 g, 24 mmol) was added dropwise (approx. addition time 30 min.). The resulting mixture was stirred at room temperature for 3 hours, filtered and the resulting solution used as such in Examples 3,4 and 5.

EXAMPLE 3

Preparation of N-ferrocenoyl-N'-3-methylbenzoyl-N'-t-butylhydrazine

To a stirred mixture of N'-3-methylbenzoyl-N'-t-butylhydrazine (0.83 g, 4.0 mmol) and 50% aqueous sodium hydroxide (0.4 g, 5.0 mmol) in toluene (30 mL) was added 7 mL of a toluene solution of ferrocenoyl chloride (Example 2), at room temperature dropwise (addition time 2 hours). After the addition was completed water is added (5 mL) and the resulting mixture allowed to stand overnight, filtered and the filtrate washed with water and dried over MgSO$_4$. Evaporation of the solvent yielded a brown oil which crystalized after rituration with hexane. N-ferrocenoyl-N'-3-methylbenzoyl-N'-t-butylhydrazine was obtained as a brown solid mp: 181°–184° C.

EXAMPLE 4

Synthesis of N-2,3-dimethylbenzoyl-N'-ferrocenoyl-N'-t-butylhydrazine

To a stirred mixture of N'-t-butyl-N-2,3-dimethylbenzoylhydrazine (0.8 g, 4.0 mmol) and K$_2$CO$_3$ (1.0 g) in toluene (30 mL) and water (5 mL) was added 3.5 mL of a toluene solution of ferrocenoyl chloride (Example 2), at room temperature dropwise. The resulting mixture is stirred at room temperature for 3 hours, filtered and the resulting yellow solid is washed with water, ether and dried to yield the product. mp: 214° C.

EXAMPLE 5

Synthesis of N-ferrocenoyl-N'-2-bromobenzoyl-N'-t-butylhydrazine at Preparation of N-Ferrocenoyl-N'-tert-butylhydrazine To a stirred suspension of tert-butylhydrazine hydrochloride (4 g, 32 mmol) in toluene (30 mL) was added, with good stirring, a solution of potassium carbonate (5 g, 36.18 mmoL) in water (10 mL). The mixture was cooled to about 5° C. and a solution of ferrocenoyl chloride (4 g, 16 mmoL) in toluene (45 mL) was added dropwise in 30 minutes. The resulting mixture was allowed to stir for 2 hours while warming to room temperature. The solid was filtered, washed sequentially with water, hexane, ethyl ether and dried to afford the product as yellow solid, melting point 145° C.

b. Preparation of N-ferrocenoyl-N'-2-bromobenzoyl-N'-tert-butylhydrazine

To a stirred mixture of N-ferrocenoyl-N'-tert-butylhydrazine (0.5 g, 1.65 mmoL) in toluene (10 mL), and potassium carbonate (0.5 g, 3.62 mmoL) in water (5 ml) was added a solution of 2-bromobenzoyl chloride (0.5 g, 1.82 mmoL) in toluene (5 mL) dropwise in 15 minutes. The resulting mixture was stirred vigorously for two hours and the solid was filtered, washed with water, ethyl ether and dried to afford product as a bright yellow solid, melting point 175° C.

TABLE I

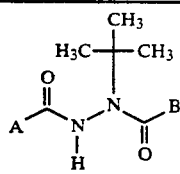

| Cpd. No. | A | B | mp (C.) |
|---|---|---|---|
| 3 | ferrocenyl | 3-Me-phenyl | 181–4 |
| 4 | 2,3-diMe-phenyl | ferrocenyl | 214 |
| 5 | ferrocenyl | 2-Br-phenyl | 175 |

EXAMPLE 6

Biological Method: Foliar Application

The compounds of the present invention were evaluated on insect species by foliar application of the compound.

A test solution containing 600 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (Triton ® X-155 surfactant from Rohm and Haas Company, Philadelphia, PA) and a modified phthalic glycerol alkyl resin (Triton ® B-1956 surfactant from Rohm and Haas Company, Philadelphia, PA) was utilized at the equivalent of 1 ounce per 100 per gal. of test solution as a surfactant.

Analogous solutions were made by serially diluting the 600 ppm test solution with water and surfactant to give concentrations of 150, 38, 10, 2.5, 0.6, 0.15 and 0.038 ppm. Not all compounds were tested at each of the several concentrations stated above. Test concentrations of a compound were selected as those most likely to differentiate dose response of a particular compound toward a particular test insect.

Initial evaluations were made on one or more of the following pests:

| Code Symbol | Common Name | Latin Name |
|---|---|---|
| AW | Southern Armyworm | Spodoptera eridania |
| BB | Mexican Bean Beetle | Epilachna varivestis |

For the Mexican Bean Beetle and Southern Armyworm test, lima bean (Phaseolus limeniss var. Woods' Prolific) seedlings in 3" pots were sprayed to run-off with the test solutions using a DeVilbiss atomizer at 20 psig. When dry, each plant was placed in a plastic box (7.5" long×5.25" wide×3.75" deep). Each box was then infested with 10 third instar larvae of either the Mexican Bean Beetle or the Southern Armyworm. The box was then sealed with a lid equipped with screened ventilation holes.

All treatments were maintained under continuous fluorescent light at 80° F. on open shelves for the course of the exposure period. Plants were watered as needed and replaced with untreated plants if they were totally consumed as was the case with ineffective treatments or untreated checks or controls. Percent mortality was determined for each test species and spray concentration at 48 and 96 hours after treatment.

Results of foliar evaluation are set forth in Table II.

TABLE II

| Cpd.No. | DOSE PPM | Insecticidal Activity | | | |
|---|---|---|---|---|---|
| | | AW[1] | AW[2] | BB[1] | BB[2] |
| 3 | 600 | 100 | 100 | 0 | 80 |
| | 38 | 20 | 100 | 0 | 0 |
| | 2.5 | 0 | 30 | 0 | — |
| 4 | 600 | 100 | 100 | 0 | 0 |
| | 38 | 20 | 100 | 0 | 0 |
| | 2.5 | 10 | 10 | 0 | — |
| 5 | 600 | 100 | 100 | 0 | 0 |
| | 38 | 0 | 0 | 0 | 10 |
| | 2.5 | 0 | 0 | 0 | — |

[1]% mortality 48 hours after treatment
[2]% mortality 96 hours after treatment

The compositions and compounds of this invention can be applied directly to the locus to be protected, as for example, the area around or upon economic plants infected with insects or to plants on which infestation is to be prevented. The compounds and compositions may be used either as contact or systemic pesticides.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

When using the compounds defined above, the method of invention is especially effective against soil insects when the active compound is applied on or in the soil in order to effect direct contact with the insects or other pests. By "pests" is meant organisms including arthropods, which in turn includes insects and acarids which organisms attack agricultural plants.

For use as pesticides, the compounds of this invention can be used a solutions, suspensions or mixtures in organic solvents or formulations. For example, they can be formulated as wettable powders, emulsifiable concentrates, dusts, granular formulations or flowable emulsifiable concentrates. In such formulations, the compounds of this invention are present at a concentration of about 0.00001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual," Allured Publishing Co., Ridgewood, N.J.

By "agronomically acceptable carrier" is meant any substance which can be utilized to dissolve, disperse or diffuse the chemical incorporated therein without impairing the effectiveness of the toxic agent and which does not create permanent damage to such environment as soil, equipment, and agronomic crops when utilized according to recommendations.

The compounds of this invention can be taken up on or mixed with a finely particled solid carrier, as for example, clays, inorganic silicates, carbonates, and silicas. Organic carriers can also be employed.

Dust concentrates are commonly made wherein compounds are present in the range of about 20 to 80%. For ultimate applications, these concentrates are normally extended with additional solid to given an active ingredient content of from 0.1 to about 20%. Granular formulations are being made using a granular or pelletized from of carrier, such as granular clays, vermiculite, charcoal or corn cobs, and may contain the active ingredient from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such material as glycerol mannitan laureate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehyde naphthalene sulfonates.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent-soluble emulsifying agent. Suitable solvents are usually water-immiscible and can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose of such application, the compound being utilized, the frequency of dissemination, and the like. For use as insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 0.05 to about 10 pounds per acre of active ingredient and for economic reasons, preferably from about 0.1 to about 2 pounds per acre.

The compounds of this invention can be utilized as the sole pesticidal agents or they can be employed in conjunction with other insecticides, acaricides, and comparable pesticides including, but not limited to acephate, acethion, acetoxon, aldicarb, aldoxycarb, aldrin, allethrin, allyxycarb, alpha-cypermethrin, hydramethylnon, amidithion, amitraz, amlure, anethol, azethion, azinphos-ethyl, azinphos-methyl, azocyclotin, Bacillus thuringiensis, BCPE, bendiocarb, bensultap, benzomate, benzoximate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chlorphoxim, chloropropylate, chlorphoxim, chlorpyrifos, chlorpyrifos methyl, chlorthiophos, cloethocarb, clofentezine, CPCBS, CPMC, crotoxyphos, crufomate, cryolite, cufraneb, cyanofenphos, cyanophos, cyanthoate, cyfluthrin, cyhexatin, cyphenothrin, cyromazine, cypermethrin, DAEP, d-phenothrin, d-trans allethrin, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlorofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, endosulfan, endothion, endrin, Entice TM, EPBP, EPN, esfenvalerate, ethiofencarb, ethion, ethoate-methyl, ethoprop, ethylan, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, fluflenoxuron, fluvalinate, fonofos, formetanate hydrochloride, formothion, fosmethilan, fosthietan, furathiocarb, furethrin, Grandlure TM, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lindane, lythidathion, malathion, mazidox, mecarbam, mecarphon, menazon, meobal, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofos, oxydisulfoton, oxythioquinox, paraoxon, parathion, Paris green, permethrin, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnel, rotenone, ryania, S-bioallethrin, dioxabenzofos, schradan, sophamide, sodium fluosilicate, sulfotep, sulprofos, tefluthrin, temephos, TEPP, terbufos, tetrachlorvinphos, tetradifon, tetramethrin, tetrasul, thallium sulfate, thiocarboxime, thiocyclam-hydrogenoxalate, thiometon, tolclofosmethyl, toxaphene, triazophos, trichloronate, trichlorfon, triflumuron, trimethacarb, and vamidothion.

Although the invention has been described with regard to its preferred embodiments, which constitute the best mode presently known to the inventors, it should be understood that various changes and modifications as would be obvious to one having ordinary skill in this art may be made without departing from the scope of the invention, which is set forth in the claims.

We claim:

1. A compound of the formula:

wherein:
A and B are independently selected from ferrocenyl, phenyl or phenyl optionally substituted with up to three substituents independently selected from $(C_1-C_6)$ alkyl, $(C_1-C_6)$ haloalkyl, $(C_1-C_6)$ alkoxy, $(C_1-C_6)$ haloalkoxy, or halogen; with the alkoxy, $(C_1-C_6)$ haloalkoxy, or halogen; with the proviso that one and only one of A and B must be ferrocenyl; and R is branched $(C_3-C_6)$ alkyl.

2. The compound of claim 1 wherein:
A and B are independently selected from ferrocenyl, phenyl or phenyl optionally substituted with up to two substituents independently selected from $(C_1-C_6)$ alkyl or halogen; and R is isobutyl, sec-butyl, tert-butyl, or neopentyl.

3. The compound of claim 1 wherein:
A and B are independently selected from ferrocenyl, phenyl or phenyl optionally substituted with up to two substituents independently selected from methyl and halogen; and R is tert-butyl.

4. The compound of claim 1 wherein:
A is ferrocenyl, B is 2-bromophenyl and R is tert-butyl.

5. The compound of claim 1 wherein:
A is ferrocenyl, B is 3-methylphenyl and R is tert-butyl.

6. The compound of claim 1 wherein:
A is 2,3-dimethylphenyl, B is ferrocenyl and R is tert-butyl.

7. An insecticidal composition comprising a pesticidially effective amount of compound of the formula:

wherein:
A and B are independently selected from ferrocenyl, phenyl or phenyl optionally substituted with up to three substituents independently selected from $(C_1-C_6)$ alkyl, $(C_1-C_6)$ haloalkyl, $(C_1-C_6)$ alkoxy, $(C_1-C_6)$ haloalkoxy, or halogen; with the proviso that one and only one of A and B must be ferrocenyl; and R is branched $(C_1-C_6)$ alkyl; and an inert carrier.

8. The composition of claim 7 wherein:
A and B are independently selected from ferrocenyl, phenyl or phenyl optionally substituted with up to two substituents independently selected from $(C_1-C_6)$ alkyl or halogen; and R is isobutyl, sec-butyl or tert-butyl.

9. The composition of claim 7 wherein:
A and B are independently selected from ferrocenyl, phenyl or phenyl optionally substituted with up to two substituents independently selected from methyl and halogen and R is tert-butyl.

10. The composition of claim 7 wherein:
A is ferrocenyl, B is 2-bromophenyl and R is tert-butyl.

11. The compound of claim 1 wherein:
A is ferrocenyl, B is 3-methylphenyl and R is tert-butyl.

12. The composition of claim 7 wherein:
A is 2,3-dimethylphenyl, B is ferrocenyl and R is tert-butyl.

13. A method of controlling insects comprising applying to said insect or insect habitat a pesticidally effective amount of a compound of the formula:

wherein:
A and B are independently selected from ferrocenyl, phenyl or phenyl optionally substituted with up to three substituents independently selected from $(C_1-C_6)$ alkyl, $(C_1-C_6)$ haloalkyl, $(C_1-C_6)$ alkoxy, $(C_1-C_6)$ haloalkoxy, or halogen; with the proviso that one and only one of A and B must be ferrocenyl; and R is branched $(C_3-C_6)$ alkyl.

14. The method of claim 13 wherein:
A and B are independently selected from ferrocenyl, phenyl or phenyl optionally substituted with up to two substituents independently selected from $(C_1-C_6)$ alkyl or halogen; and R is isobutyl, sec-butyl or tert-butyl.

15. The method of claim 13 wherein:
A and B are independently selected from ferrocenyl, phenyl or phenyl optionally substituted with up to two substituents independently selected from methyl and halogen and R is tert-butyl.

16. The method of claim 13 wherein:
A is ferrocenoyl, B is 2-bromophenyl and R is tert-butyl.

17. The method of claim 1 wherein:
A is ferrocenyl, B is 3-methylphenyl and R is tert-butyl.

18. The method of claim 1 wherein:
A is 2,3-dimethylphenyl, B is ferrocenyl and R is tert-butyl.

* * * * *

UNITED STATES PATENT AND TRADEMARK OFFICE
CERTIFICATE OF CORRECTION

PATENT NO. : 5,075,471
DATED : December 24, 1991
INVENTOR(S) : Enrique L. Michelotti, Dat P. Le, Glenn R. Carlson, Anne R. Egan It is certified that error appears in the above-identified patent and that said Letters Patent is hereby corrected as shown below:

Column 15,

Claim 1, lines 28 and 29 "$(C_1-C_6)$ haloalkoxy, or halogen; with the alkoxy, $(C_1-C_6)$ haloalkoxy, or halogen; with the proviso" should read:

--$(C_1-C_6)$ haloalkoxy, or halogen; with the proviso--

Signed and Sealed this

Twenty-fifth Day of May, 1993

Attest:

MICHAEL K. KIRK

Attesting Officer

Acting Commissioner of Patents and Trademarks